(12) United States Patent
Langdale et al.

(10) Patent No.: US 9,687,274 B2
(45) Date of Patent: Jun. 27, 2017

(54) MAGNETIC VAGINAL DILATOR

(71) Applicant: VUVATECH LLC, Sarasota, FL (US)

(72) Inventors: Tara Leann Langdale, Sarasota, FL (US); Robert James Smithson, Sarasota, FL (US)

(73) Assignee: VuVatech LLC, Sarasota, FL (US)

(*) Notice: Subject to any disclaimer, the term of this patent is extended or adjusted under 35 U.S.C. 154(b) by 0 days.

(21) Appl. No.: 14/676,533

(22) Filed: Apr. 1, 2015

(65) Prior Publication Data

US 2015/0282838 A1 Oct. 8, 2015

Related U.S. Application Data

(60) Provisional application No. 61/975,512, filed on Apr. 4, 2014.

(51) Int. Cl.
| | |
|---|---|
| *A61M 29/00* | (2006.01) |
| *A61B 17/42* | (2006.01) |
| *A61M 29/02* | (2006.01) |
| *H01F 7/02* | (2006.01) |
| *A61B 17/52* | (2006.01) |
| *A61B 17/00* | (2006.01) |

(52) U.S. Cl.
CPC ............ *A61B 17/42* (2013.01); *A61M 29/02* (2013.01); *H01F 7/0221* (2013.01); *H01F 7/0294* (2013.01); *A61B 17/52* (2013.01); *A61B 2017/00876* (2013.01); *A61M 29/00* (2013.01); *A61M 2207/00* (2013.01)

(58) Field of Classification Search
CPC .. A61N 2005/0644; A61N 2/002; A61N 2/06; A61N 5/0613
See application file for complete search history.

(56) References Cited

U.S. PATENT DOCUMENTS

| | | | |
|---|---|---|---|
| 4,011,961 A | 3/1977 | Widen et al. | |
| 4,587,956 A | 5/1986 | Griffin | |
| 6,344,021 B1 * | 2/2002 | Juster | A61N 2/06 600/15 |
| 6,482,147 B2 | 11/2002 | Knoll-Ewers | |
| 6,632,168 B2 * | 10/2003 | Roberts | A61N 2/008 600/15 |
| 2004/0002626 A1 | 1/2004 | Feld et al. | |
| 2007/0244388 A1 | 10/2007 | Sato et al. | |

(Continued)

OTHER PUBLICATIONS

International Search Report with Written Opinion dated Aug. 31, 2015 in Application No. PCT/US15/23996, 14 pages.

(Continued)

*Primary Examiner* — Christine H Matthews
(74) *Attorney, Agent, or Firm* — Shook, Hardy & Bacon, L.L.P.

(57) ABSTRACT

Aspects of the present invention are related to magnetic medical devices for the treatment of chronic medical conditions such as Vulvodynia, Vaginismus, Vaginal Stenosis, Vaginal Atrophy, among others. The magnetic medical device in accordance with the present invention is of a generally elongated shape having an ogive top end, a middle portion of an active diameter, and a bottom end of a passive diameter. The magnetic medical device has an array of magnets within, where the magnets generate a negative magnetic field adjacent to an external surface of the magnetic medical device.

19 Claims, 8 Drawing Sheets

(56) References Cited

U.S. PATENT DOCUMENTS

| | | |
|---|---|---|
| 2008/0139875 A1 | 6/2008 | Tracey et al. |
| 2010/0145147 A1 | 6/2010 | Pinsky et al. |
| 2011/0034809 A1 | 2/2011 | Eberle et al. |
| 2012/0136287 A1 | 5/2012 | Barnard et al. |
| 2012/0245403 A1* | 9/2012 | Martinez ................. A61N 1/40 600/13 |
| 2013/0041229 A2 | 2/2013 | Hahn et al. |
| 2013/0066136 A1* | 3/2013 | Palese ................... A61B 17/52 600/11 |
| 2013/0211180 A1* | 8/2013 | Tothne Kovesdi .... A61N 2/002 600/9 |

OTHER PUBLICATIONS

International Preliminary Report on Patentability dated Oct. 13, 2016 for International Patent Application No. PCT/US2015/023996, 10 pages.

* cited by examiner

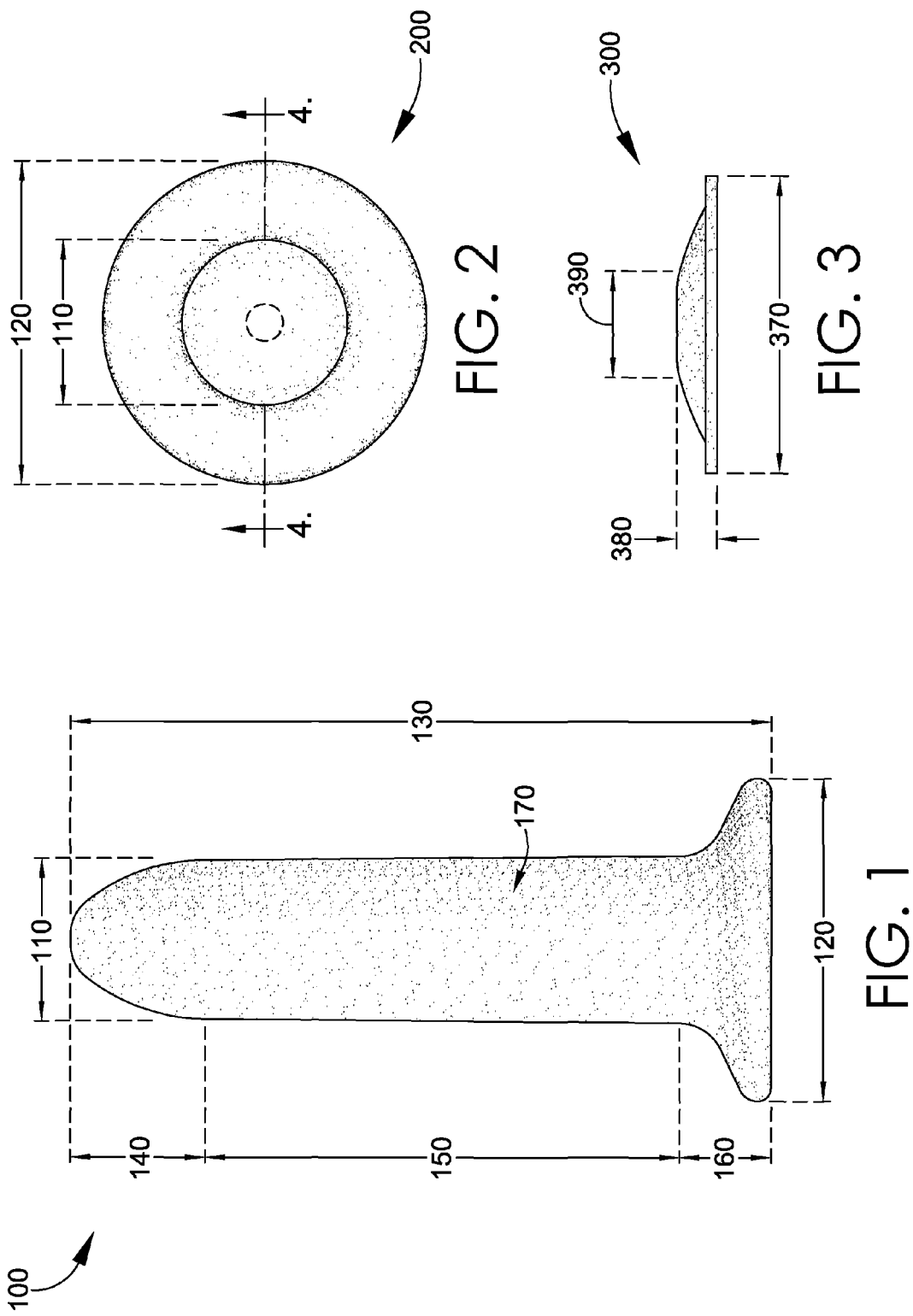

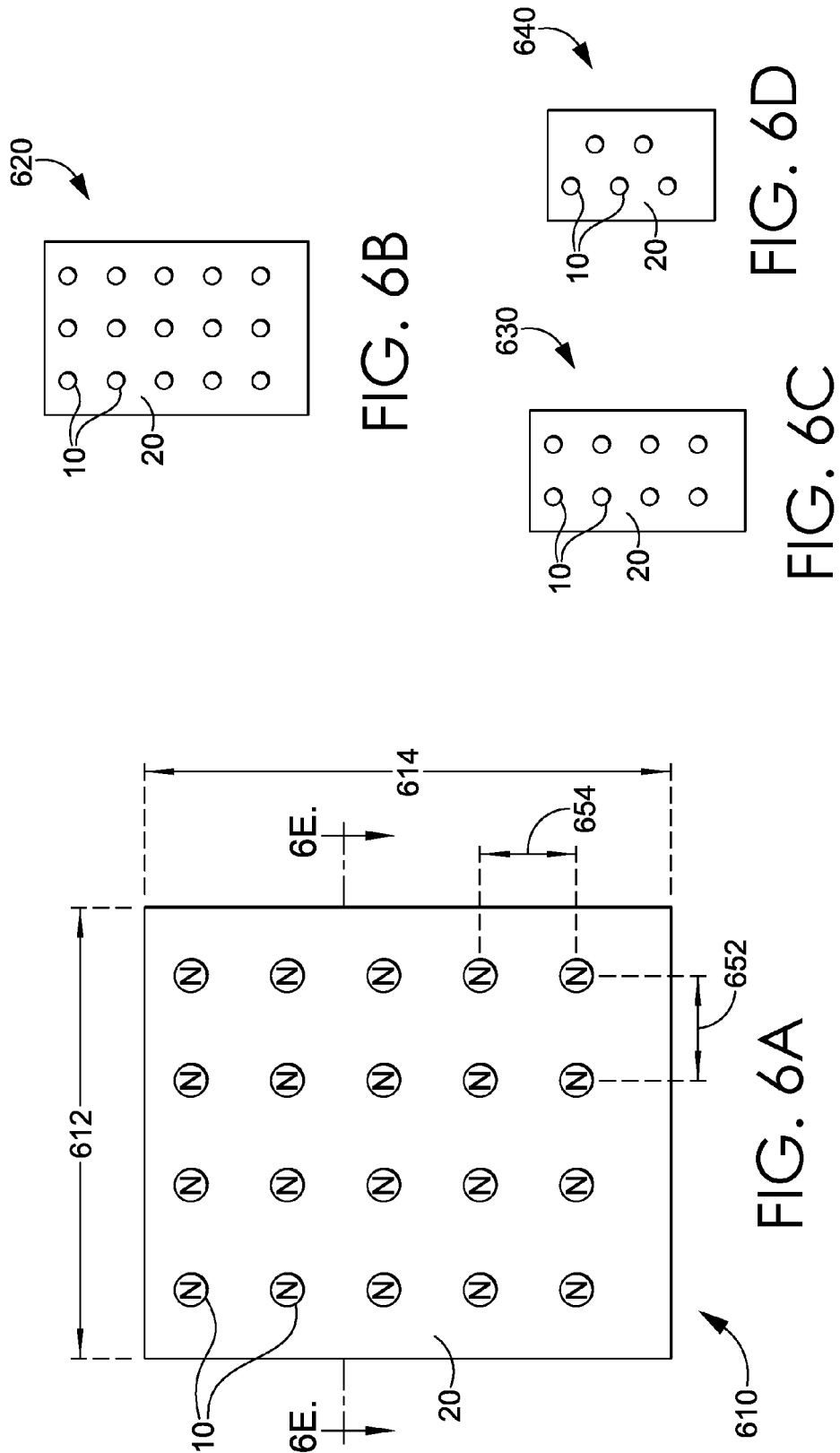

MAGNETIC VAGINAL DILATOR

CROSS-REFERENCE TO RELATED APPLICATIONS

This application claims the benefit of U.S. Provisional Application Ser. No. 61/975,512 filed on Apr. 4, 2014.

FIELD OF THE INVENTION

The present invention relates generally to a magnetic medical device for treatment of chronic conditions related to female genital organs such as Vulvodynia or vaginal nerve pain, Vaginismus, vaginal stenosis, vaginal atrophy, menopause, and dyspareunia, among others.

BACKGROUND

Vulvodynia is a chronic pain syndrome without an identifiable cause. Vulvodynia affects the vulvar area, which consists of the external genital organs of a female reproductive system. More specifically, the vulvar area comprises anatomical structures including labia majora, mons pubis, labia minora, clitoris, bulb of vestibule, vulval vestibule, greater and lesser vestibular glands, external urethral orifice and the opening of the vagina. These anatomical structures are richly innervated, resulting in a heightened touch sensation. Symptoms of Vulvodynia may include burning, stinging, irritation, and/or sharp pain. Such symptoms may be constant, intermittent, or occur only upon touch, and may last for weeks, months, or even years. Although a specific cause for Vulvodynia has not been medically identified, some probable causes may include sexual activity, tampon use, genetic predisposition, or prolonged application of pressure such as, for example, when engaged in an activity that requires prolonged sitting or riding.

Vaginismus is a condition that impedes vaginal penetration due to involuntary vaginal muscle spasms that cause pain. The vaginal muscles believed to be involved in the muscle spasms are the pubococcygenus muscle ("PC muscle"), levator ani, bulbocavernous, circumvaginal, and perivaginal muscles.

Vaginal stenosis and vaginal atrophy are related to the reduction in resiliency of the vaginal canal and/or inflammation of the vagina. Vaginal atrophy in particular, is directed to the inflammation of vaginal tissues due to a hormonal imbalance, such as a decrease in estrogen levels, particularly during menopause. Dyspareunia is another related condition characterized by painful sexual intercourse.

Other conditions related to vulvar tissue inflammation leading to vaginal discomfort may include: injuries to or irritation of nerve endings in the vulva, increased nerve fiber density in the vulvar vestibule, high levels of inflammatory response triggers in the vulvar tissue due to trauma and/or infection, hormonal imbalance, genetic susceptibility to chronic vestibular inflammation, genetic susceptibility to chronic widespread pain, hypersensitivity to yeast or other types of infections, pelvic floor muscle weakness or spasms, and back or spinal surgery.

The aforementioned vaginal chronic conditions affect a large female population. For instance, about 23% of women suffering from at least one of these chronic conditions are under the age of 25, about 54% of women suffering from at least one of these chronic conditions are between ages 26-35, about 19% of women suffering from at least one of these chronic conditions are between ages 36-50, and about 4% of women suffering from at least one of these chronic conditions are over the age of 51.

As the causes of many of these conditions, particularly Vulvodynia and Vaginismus, are not identified or well-known, sufferers of such conditions are often frustrated in their search for a treatment or cure. Especially because, often times, the pain suffered by these females can move beyond the physical realm and can have potentially damaging psychiatric effects including anxiety, depression, melancholia, and others. As such, there exists a need for an effective treatment of these conditions that is minimally invasive and relatively easy to manufacture, as presented below.

SUMMARY OF THE INVENTION

In one embodiment in accordance with the present invention, there is provided a magnetic medical device that is configured to be used as a vaginal dilator. The magnetic medical device comprises at least a shell member, a magnetic layer, and a cap member. The shell member is defined by an external surface and an interior surface, the interior surface defining a void or cavity within the shell member. The magnetic layer comprises a polymer sheet material sized to be enclosed within the cavity defined within the shell member. The polymer sheet material comprises a plurality of magnets adhered thereon, wherein the plurality of magnets are arranged in a configuration for radially directing a magnetic field in relation to the length of the magnetic medical device. The cap member is configured to fit within the shell member to enclose the sheet material comprising the magnets.

In another embodiment of the present invention, there is provided a method for treating a patient suffering from Vulvodynia, the method comprising the steps of: (1) providing a set of variably sized magnetic medical devices shaped to work as vaginal dilator members; (2) determining a suitably-sized magnetic medical device from the set of variably sized magnetic medical devices; (3) inserting the suitably-sized magnetic medical device into the vaginal canal of the patient; (4) maintain contact between the magnetic medical device and the tissue surface of the vaginal canal for a period of about 10 minutes to about 30 minutes, up to 7 times a day.

BRIEF DESCRIPTION OF THE SEVERAL VIEWS OF THE DRAWINGS

Illustrative embodiments of the technology are described in detail below with reference to the attached drawing figures, wherein:

FIG. 1 depicts a shell component of a magnetic medical device in accordance with embodiments of the present invention;

FIG. 2 depicts a top view of the magnetic medical device in accordance with embodiments of the present invention;

FIG. 3 depicts a cap component of the magnetic medical device in accordance with embodiments of the present invention;

FIG. 6A depicts a magnet array substrate film for the magnetic sleeve for the embodiment depicted in FIG. 5A;

FIG. 6B depicts a magnet array substrate film for the magnetic sleeve for the embodiment depicted in FIG. 5B;

FIG. 6C depicts a magnet array substrate film for the magnetic sleeve for the embodiment depicted in FIG. 5C;

FIG. 6D depicts a magnet array substrate film for the magnetic sleeve for the embodiment depicted in FIG. 5D;

DETAILED DESCRIPTION

Figure 4:
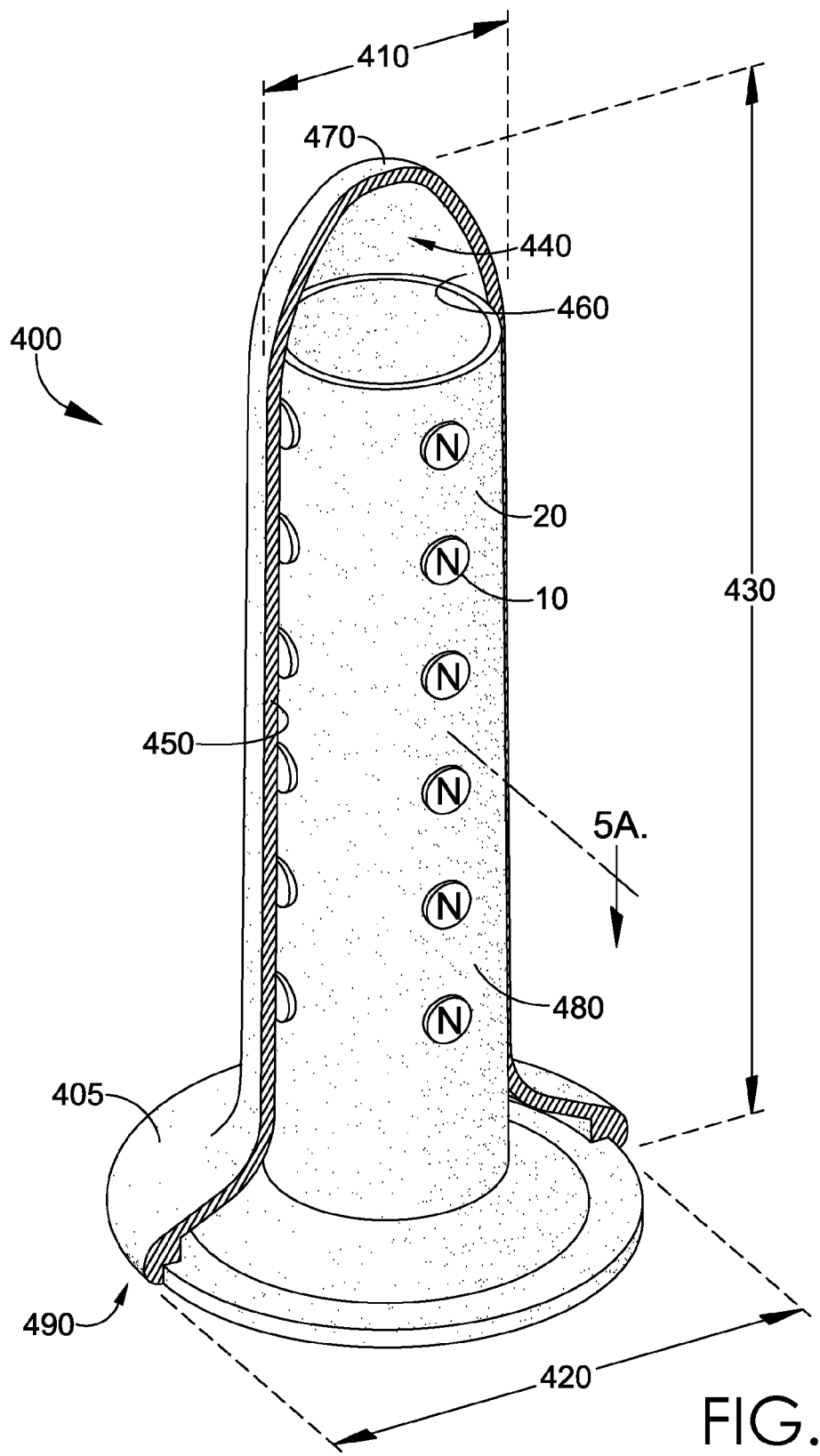
FIG. 4 depicts a cross-sectional view along the line 4-4 in FIG. 2, in accordance with embodiments of the present invention.

The subject matter of the present technology is described with specificity herein to meet statutory requirements. However, the description itself is not intended to define the technology, which is what the claims do. Rather, the claimed subject matter might be embodied in other ways to include different components, steps, or combinations of components or steps similar to the ones described in this document, in conjunction with other present or future technologies. Moreover, although the term "step" or other generic term might be used herein to connote different components or methods employed, the terms should not be interpreted as implying any particular order among or between various steps herein disclosed unless and except when the order of individual steps is explicitly described.

The principle of operation of the present invention revolves around the generation of a negative magnetic field in the vicinity of the affected area. The negative magnetic field acts to attract positively charged ions, impeding the flow of a majority of positively charged ions along proximate nerves to the brain, thereby reducing sensation in the affected area. Additionally, there is a direct correlation between the length of time the magnetic field is in place, and its effectiveness for reducing symptoms related to the chronic conditions like Vulvodynia, Vaginismus, and other similar chronic conditions affecting the vaginal area.

In general, the present invention is a magnetic medical device to be used as a vaginal dilator. The vaginal dilators in accordance with the present invention provide a non-invasive, reusable, homeopathic medical device that acts by stimulating blood flow in the affected tissues by exposing the affected tissues to a negative magnetic field. The blood flow increase can improve the circulation of oxygen and nutrients to the affected area, which in turn provides relief from the symptoms that accompany the aforementioned chronic conditions. The vaginal dilators in accordance with the present invention comprise a generally elongated shape to fit comfortably inside the vaginal cavity of a female patient. Due to the wide range of patients having different physical characteristics, the vaginal dilators in accordance with the present invention can be manufactured in a range of sizes to fit as needed. The vaginal dilators can range in length, for example, between 1.5 inches—8 inches, and can range in diameter between 0.5 inches-1.5 inches. More specifically, the vaginal dilators in accordance with the present invention may be manufactured according to the size specifications presented below in Table 1.

TABLE 1

Different approximate size configurations for the vaginal dilators in accordance to the present invention:

| Unit | Diameter (inches) | Length (inches) |
|---|---|---|
| 1 | 0.5 | 2.75 |
| 2 | 0.75 | 3.5 |
| 3 | 1 | 4.5 |
| 4 | 1.25 | 5.5 |
| 5 | 1.5 | 6.25 |

Each of the vaginal dilators described in Table 1 will be described in reference to the figures presented in accordance with the present invention. FIG. 1 depicts a shell component 100 of the magnetic medical device in accordance with the present invention, which gives the magnetic medical device its overall shape. The shell component 100 comprises a generally elongated cylindrical shape having a top/first end 140, a middle portion 150, and a bottom/second end 160. The middle portion 150 comprises a first diameter 110. The top/first end 140 is ogive, generally tapering in from the first diameter 110. The second end 160 generally tapers out to a second diameter 120, wherein the second diameter 120 is bigger than the first diameter 110. Further, the shell component 100 comprises an outer surface 170 and an inner surface (not shown). The inner surface of the shell component 100 defines a cavity within the shell component, the cavity (not shown) comprising an opening (not shown) at the bottom/second end 160.

The outer surface 170 is smooth, to aid in the use and comfort during use of the magnetic medical device in accordance with the present invention. Materials suitable for the present invention include FDA-approved thermoplastic materials, glass, or medical-grade metals/alloys that may be suitable for use in accordance with the present invention. For example, a preferred material for use in accordance with the present invention may a medical-grade polycarbonate material that is injection molded into the appropriate shape for use in the magnetic medical device in accordance with the present invention.

FIG. 2 depicts a top view 200 of the shell 100. As seen from the top view 200 in FIG. 2, the shell component 100 comprises two main diameters and an ogive top/first end 140. The ogive top/first end 140 allows for a comfortable, gradual insertion of the magnetic medical device into the vaginal canal of a female patient. The first diameter 110 is the active diameter and determines the course of treatment for the female patient. For instance, the first diameter 110 comprises the length 150 of the magnetic medical device, which is inserted into the vaginal canal of the female patient. The magnetic medical device gradually tapers out from the first diameter 110 to a second diameter 120 at the bottom/second end 160. The second diameter 120 is a passive diameter provided for safety and comfortable handling of the magnetic medical device in accordance with the present invention. As described above, the magnetic medical device in accordance with the present invention is used as a vaginal dilator, and since its use requires the insertion of the magnetic medical device into the vaginal canal of the female patient, the second diameter 120 allows for easy grip of the magnetic medical device during insertion and extraction of the magnetic medical device, while also safely preventing the magnetic medical device from being inserted beyond its intended reach.

FIG. 3 depicts a cap component 300 in accordance with the present invention. The cap component 300 is configured to precisely fit the opening at the bottom/second end 160 of the shell component 100. The precision fit of the cap 300 is important for sealing a substrate film with a magnet array, within the cavity of the shell component, as will be described herein. The cap component may be adhesively or ultrasonically sealed to the shell component, once assembly of the magnetic medical device is completed. The tight seal formed between the shell component 100 and the cap 300 facilitates the prevention of contaminants from entering the cavity of the shell component 100, thereby preventing contamination of the film substrate and magnets disposed therein. Maintaining sanitary conditions within the cavity is important, as the magnetic medical device in accordance with the present invention is reusable and may be subjected to multiple wash and dry cycles with soap and water, or other suitable cleaning solutions.

Moving now to FIG. 4, FIG. 4 shows a cross-sectional view of a shell component 405, corresponding to fully assembled magnetic medical device 400. As seen in FIG. 4, the shell component 405 generally presents an elongated cylindrical shape and comprises an inner surface 460 and an outer surface 470, wherein the inner surface defines a cavity 440 within the shell component 405. Further, as described in reference to FIG. 1, the magnetic medical device 400 has an active diameter 410 substantially throughout its length 430 and a passive diameter 420 at its bottom end 490, wherein the active diameter 410 is smaller than the passive diameter 420.

Furthermore, the inner surface 460 and the outer surface 470 are separated by a thickness 450. The thickness 450 of the shell component 405 ranges from 0.050 inches to 0.10 inches. Preferably, the thickness 450 of the shell component 405 is 0.07 inches. The thickness 450 of the shell component 405 is configured to allow the magnetic medical device to be sturdy, durable, and firm, while at the same time, allowing a magnetic field induced by the magnetic sleeve 480, to be active on the outer surface of the magnetic medical device 400. As further shown in FIG. 4, the magnetic sleeve 480 is comprised of a polymer substrate film 20 and a plurality of magnets 10. The plurality of magnets 10 are arranged in an array that is optimized for a maximum magnetic field effect on the vaginal tissues that are subject to treatment when the magnetic medical device 400 is inserted into the vaginal canal of a female patient. For example, in this particular embodiment, the magnets are arranged in five rows to provide a magnetic field substantially throughout the length 430 of the magnetic medical device 400.

Figure 5A:
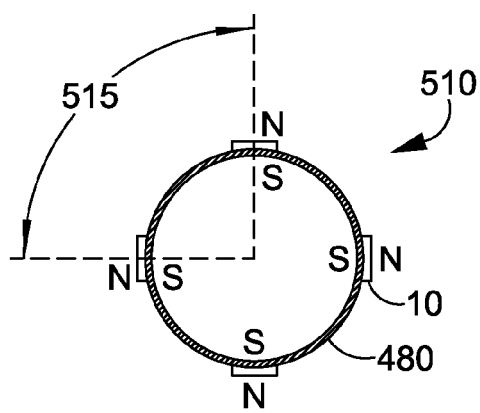
FIG. 5A depicts a cross-sectional view of the magnetic sleeve along the line 5-5 in FIG. 4, in accordance with an embodiment of the present invention.

FIG. 5A depicts a cross-section of the magnetic sleeve 480 along a perpendicular plane defined by the line 5A in FIG. 4. The cross-section of the magnetic sleeve 510 may have the magnets 10 arranged in an array of four magnets 10 per row. In order to evenly distribute the magnetic field along the inner surface 460 and outer surface 470 of the magnetic medical device 400, the four magnets 10 in each row may be separated by a 90° arc 515. Additionally, the magnets 10 are arranged so that the negative/north pole of each and every magnet 10, in the array of magnets 10, is always facing (outward) the inner surface 460 of the magnetic medical device 400, when the magnetic sleeve is inserted into the cavity 440. This allows for an evenly distributed negative magnetic field to be emanated throughout the outer surface 470 of the magnetic medical device 400. The negative magnetic field (not shown), is believed to combat inflammation and it is believed to aid in the dissolution of troublesome calcium mineral deposits that may be the cause of the acute pain symptoms related to the health conditions such as Vaginismus and Vulvodynia. Furthermore, the negative magnetic field is believed to relieve symptoms by stimulating blood circulation, oxygenation, and alkalization of the treated vaginal tissues.

Figure 5B:
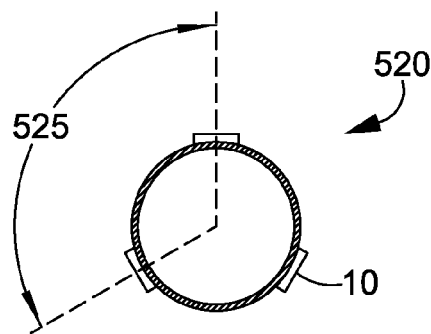
FIG. 5B depicts a cross-sectional view of the magnetic sleeve of a second embodiment in accordance with the present invention.

FIG. 5B depicts a cross-section of a magnetic sleeve 520 according to a different embodiment from the one depicted in FIG. 5A. In the embodiment of FIG. 5B, there may be three magnets 10 in each row of the array, wherein the magnets may be separated by a 120° arc 525 for even distribution of the negative magnetic field. This magnetic sleeve may be suitable for a magnetic medical device 400 having a smaller active diameter 410 than a magnetic medical device 400 having an active diameter 410 configured to enclose the magnetic sleeve 510 of FIG. 5A. For example, the magnetic sleeve 510 may be suitable for a magnetic medical device 400 comprising an active diameter 410 of 1.5 inches, while the sleeve 520 may be suitable for a magnetic medical device 400 comprising an active diameter 410 of 1.25 inches or an active diameter of 1 inch.

Figure 5C:
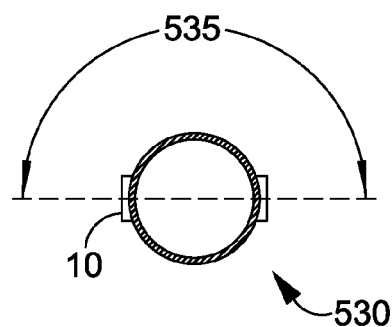
FIG. 5C depicts a cross-sectional view of the magnetic sleeve of a third embodiment in accordance with the present invention.

FIG. 5C depicts a cross-section of yet another magnetic sleeve 530. In the embodiment of FIG. 5C, there may be 2 magnets 10 in each row of the array, wherein the magnets 10 may be separated by a 180° arc 535 for even distribution of the negative magnetic field. The magnetic sleeve 530 may, for example, be suited for a magnetic medical device 400 having an active diameter 410 of 0.75 inches.

Figure 5D:
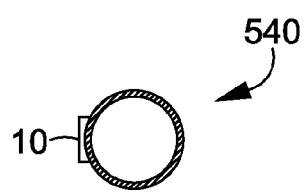
FIG. 5D depicts a cross-sectional view of the magnetic sleeve of a fourth embodiment in accordance with the present invention.

Finally, FIG. 5D depicts a cross-section of an additional embodiment for a magnetic sleeve 540, in which only one magnet 10 is arranged per row for an even distribution of a negative magnetic field. The magnetic sleeve 540 may, for example, be suited for a magnetic medical device 400 having an active diameter 410 of 0.5 inches.

FIGS. 6A to 6D depict the magnet arrays for each of the sleeve cross-sections depicted in FIGS. 5A to 5D, respectively. For instance, substrate film 20 may have a height 614 and a width 612, wherein the height 614 may be equal to the width 612, or in the alternative, the height 614 may be different than the width 612. The substrate film may be printed with a magnet array guide showing a precise location for each magnet 10 to be affixed to the substrate film 20 (not shown). For example, magnet array 610 may comprise five rows with four magnets 10 per row. Each magnet 10 in the array 610 may be separated from the other magnets 10 in the array 610 by a distance 652 along the width 612 of the substrate film 20, and a distance 654 along the height 614 of the substrate film 20. The distance 652 and the distance 654 may be equal, or in the alternative, the distance 652 may be different than the distance 654. FIG. 6B shows a substrate film 20 with an array 620 of magnets 10 arranged in five rows with three magnets 10 per row. FIG. 6C depicts a substrate film 20 with an array 630 of magnets 10 arranged in four rows with two magnets 10 per row. Finally, FIG. 6D shows a substrate film 20 with an array 640 of magnets 10 arranged in five rows with one magnet 10 per row. The uniqueness of the array 640 is that the single magnets per row are arranged in a staggered configuration for allowing spacing between magnets 10 when substrate film 20 is rolled into sleeve 540, prior to insertion of sleeve 540 into the internal cavity of shell 405.

Figure 6E:
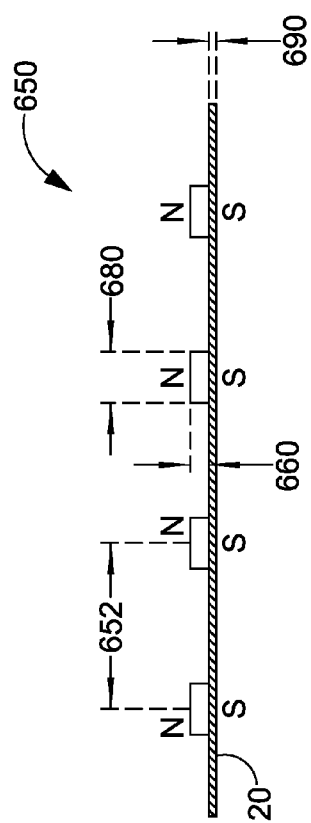
FIG. 6E depicts a cross-sectional view along the line 6E-6E in FIG. 6A.

FIG. 6E is a cross-section 650 of the substrate film 20 for the array 610 depicted in FIG. 6A, along the line 6E-6E. As seen throughout the figures, the magnets 10 may be circular, therefore having an overall cylindrical shape. However, the magnets 10 may comprise any shape suitable in accordance with embodiments of the present invention. For example, the magnets 10 may have a polygonal shape (triangle, square, pentagon, etc.) or the magnets 10 may have an organic shape such, for example, a heart, clover, etc.

For simplicity, embodiments of the present invention will be described with magnets 10 having a cylindrical shape with a height 660 and a diameter 680. The height 660 and the diameter 680 of each magnet 10, define an overall size for each magnet 10. In accordance to aspects of the present invention, each magnet 10 may have a diameter ranging between 0.1 and 0.5 inches, and a height ranging between 0.05 and 0.1 inches. Preferably, each magnet 10 in accordance with the present invention has a diameter of 0.25 inches and a height of 0.0625 inches. The magnets 10 in accordance with the present invention may be any type of magnet suitable for medical use. For example, the magnets 10 in accordance the present invention may comprise Neodymium earth magnets. More particularly, the Neodymium earth magnets used in accordance with the present invention may comprise N35 grade magnets having a magnetic field strength of 12,300 Gauss of 1.23 Tesla. Depending on a desired strength of magnetic field, other magnet grades with varying strengths may be used. In other embodiments, a mixture of magnet grades may be used in other to create the appropriate magnetic field deemed necessary for treatment of a particular condition, or a particular patient's needs.

FIG. 6E further illustrates a cross-section of substrate film 20. Substrate film 20 may comprise any neutral thermoplastic polymer material suitable for embodiments of the present invention. The substrate film 20 preferably comprises a semi-rigid thermoplastic film material. For example, the substrate film 20 may be a polyester film. The polyester film may, for example be a clear Melinex® film available from DuPont. The substrate film 20 may have a thickness ranging between 0.002 inches and 0.008 inches. Preferably, the substrate film 20 comprises a thickness of 0.005 inches. The thickness of the substrate film 20 gives the substrate film 20 a certain amount of rigidity, which pushes the magnets 10 against the inner surface 460 of the shell component 405 when the magnetic sleeve is inserted into the cavity 440. Each substrate film 20 may be laser printed with a magnet array map prior to affixing the magnets 10 to the substrate film 20 to ensure accurate placement of the magnets 10. The magnets 10 may be adhesively affixed to the substrate film 20 using suitable adhesives. For example, a suitable adhesive for use in accordance with the present invention has been found to be adhesive #4032 sold by 3M®. The adhesive used in accordance with aspects of the present invention must be strong enough to hold the bond between the magnet and the substrate film 20, preferably for the life of the magnetic medical device 400. In some instances, the magnets 10 may be provided with an adhesive already applied thereon, so as to facilitate affixation of the magnets 10 to the film 20.

Figure 7:
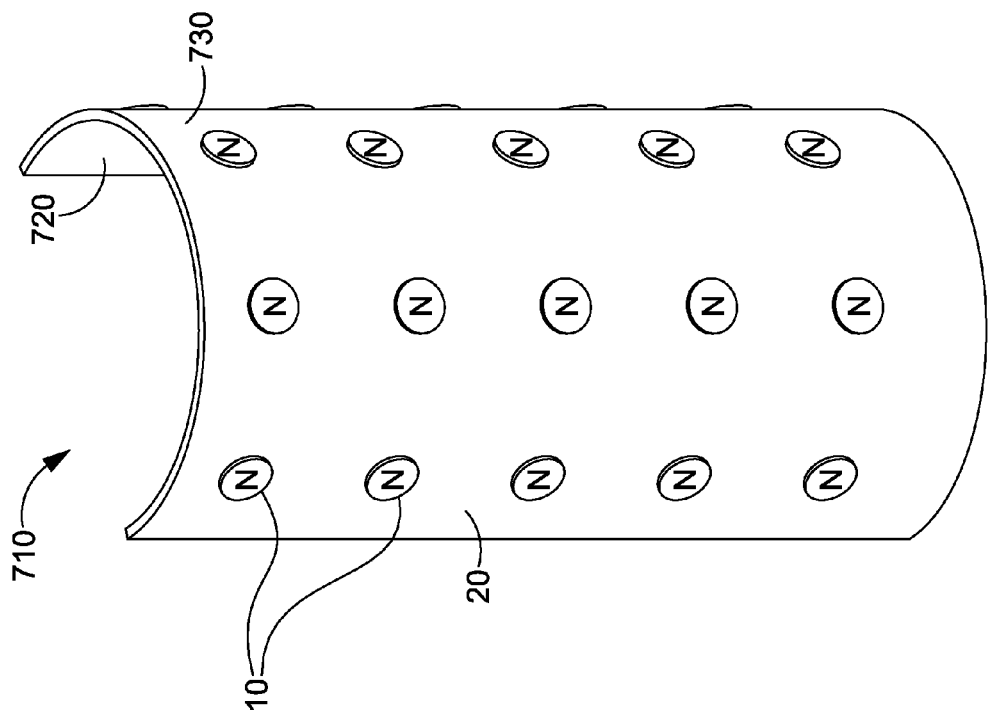
FIG. 7 depicts how a magnet array substrate film is rolled to form the magnetic sleeve inside the magnetic medical device in accordance with the present invention.

FIG. 7 depicts a partially formed magnetic sleeve 710 from a substrate film 20 with the respective array of magnets 10. As depicted in FIGS. 6A to 6D, the substrate film 20 is preferably a flat, quadrilaterally-shaped film, with a magnet array map printed thereon. One or more magnets 10 are adhered to the film, wherein each of the one or more magnets 10 is configured so that its (negative) north pole is facing in a first direction. Preferably, the one or more magnets 10 are adhered so that the (negative) north pole of each magnet 10 is facing outwardly when adhered to the substrate film 20, as will be described in more detail herein. The substrate film 20 having the one or more magnets 10 affixed thereon, is rolled into a cylinder, so that the one or more magnets 10 end up on the outer surface 730 of the magnetic sleeve 710, and not on the inner surface 720 of the magnetic sleeve 710. The substrate film 20 is rolled just enough to form a magnetic sleeve 710 that will fit within the appropriate cavity of an appropriate shell component that is configured to fit the magnetic sleeve 710. Once inserted into the appropriate cavity of the appropriate shell component configured to fit the magnetic sleeve 710, the substrate film 20 is allowed to partially unravel to conform to the appropriate cavity of the appropriate shell component that is configured to fit the magnetic sleeve 710. As such, the substrate film 20 pushes the magnets against the inner surface of the shell component. In this regard, the negative magnetic field generated by the one or more magnets 10 have substantially no loss in strength due to the barrier created by the thickness of the shell component. To this end, a magnetic medical device providing a suitably strong negative magnetic field (magnetic North or medical North) for the treatment of conditions such as Vulvodynia and Vaginismus, among others, is provided.

Figure 8:
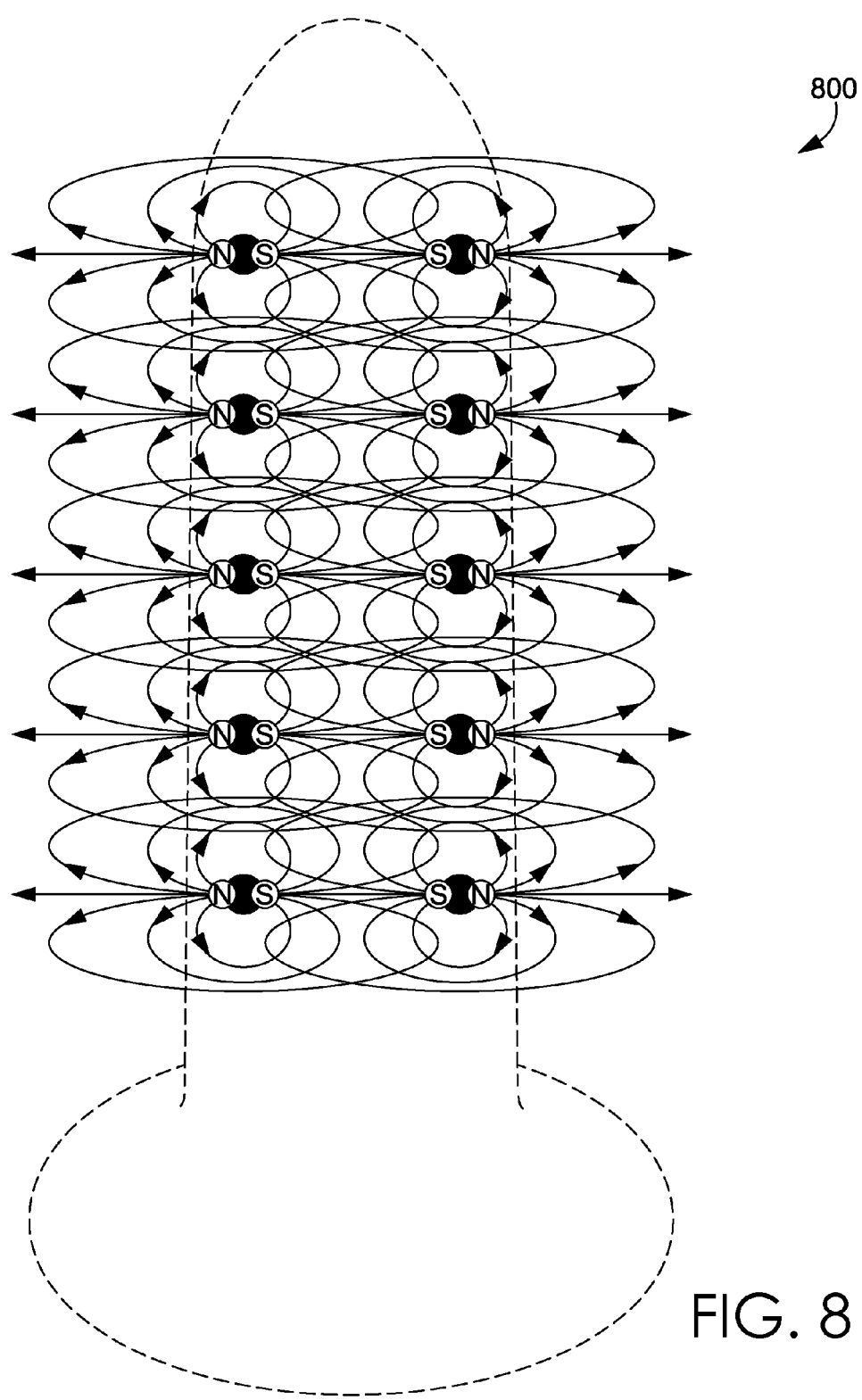
FIG. 8 depicts an active magnetic field generated by the magnetic sleeve outside and inside of the magnetic medical device.

FIG. 8 depicts the negative magnetic field 800 created by the one or more magnets 10 when arranged in a magnetic sleeve within the magnetic medical device in accordance with the present invention. It is contemplated within the scope of the present invention to include other magnetic field generating components in lieu of the one or more magnets 10. For instance, one or more electromagnets may be employed to generate a magnetic north field similar to the illustrated negative magnetic field 800.

The magnetic field 800 created by the magnetic medical device (vaginal dilator) in accordance with the present invention, provides a holistic, non-invasive treatment for chronic conditions such as Vulvodynia and Vaginismus, by increasing blood flow within the vaginal tissues of a vaginal canal, to which the magnetic medical device is inserted. Additionally, the negative magnetic field 800 acts to attract positively charged ions (pain conductors), thereby impeding the vaginal nerves from communicating pain signals to the brain. The length of treatment and observation of positive results may vary from patient to patient, depending on the extent of damage and/or inflammation of the vaginal tissues.

Figure 9:
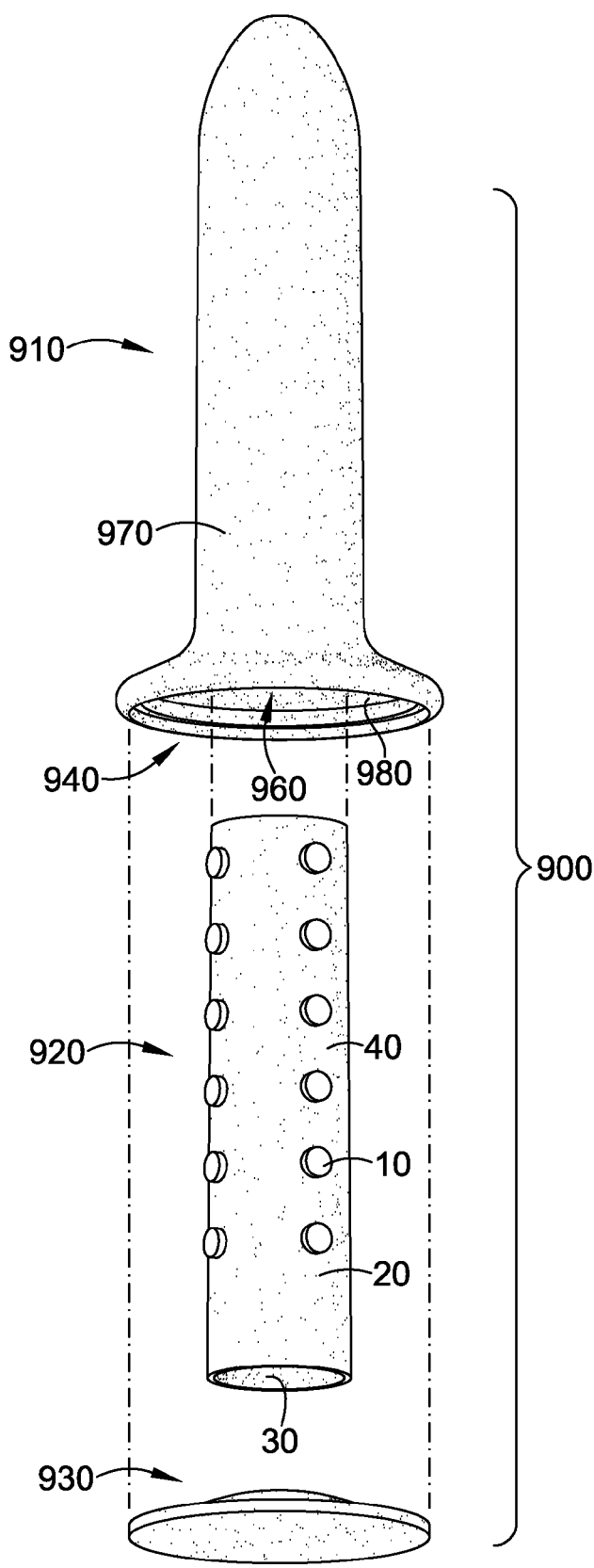
FIG. 9 depicts a deconstructed view of a magnetic medical device in accordance with the present invention.

FIG. 9 depicts a deconstructed magnetic medical device 900 to show how the magnetic medical device 900 is assembled. For instance, magnetic medical device 900 comprises a shell component 910 comprising an outer surface 970 and an inner surface 980, the inner surface 980 defining a cavity 960 within the shell component 910. Inserting a magnetic sleeve 920 comprising a substrate film 20 with one or more magnets 10 affixed to the outer surface of the magnetic sleeve 40 and not the inner surface of the magnetic sleeve 30. The one or more magnets 10 are arranged on the magnetic sleeve 920 according to a predetermined pattern for optimal generation of a radially outwardly-facing negative magnetic field. Finally, sealing the magnetic sleeve 920 into the cavity 960 of the shell component 910 by placing a cap component 930 onto the opening 940 of the cavity 960. The cap component 930 is configured to tightly fit the opening 940 of the cavity 960 and can be adhesively, ultrasonically, or heat bonded to the shell component 910, wherein the bonding method may be chosen according to the materials used for the manufacture of the shell component 910 and cap component 930. Preferably, the shell component 910 and the cap component 930 are comprised of the same material.

Figure 10:
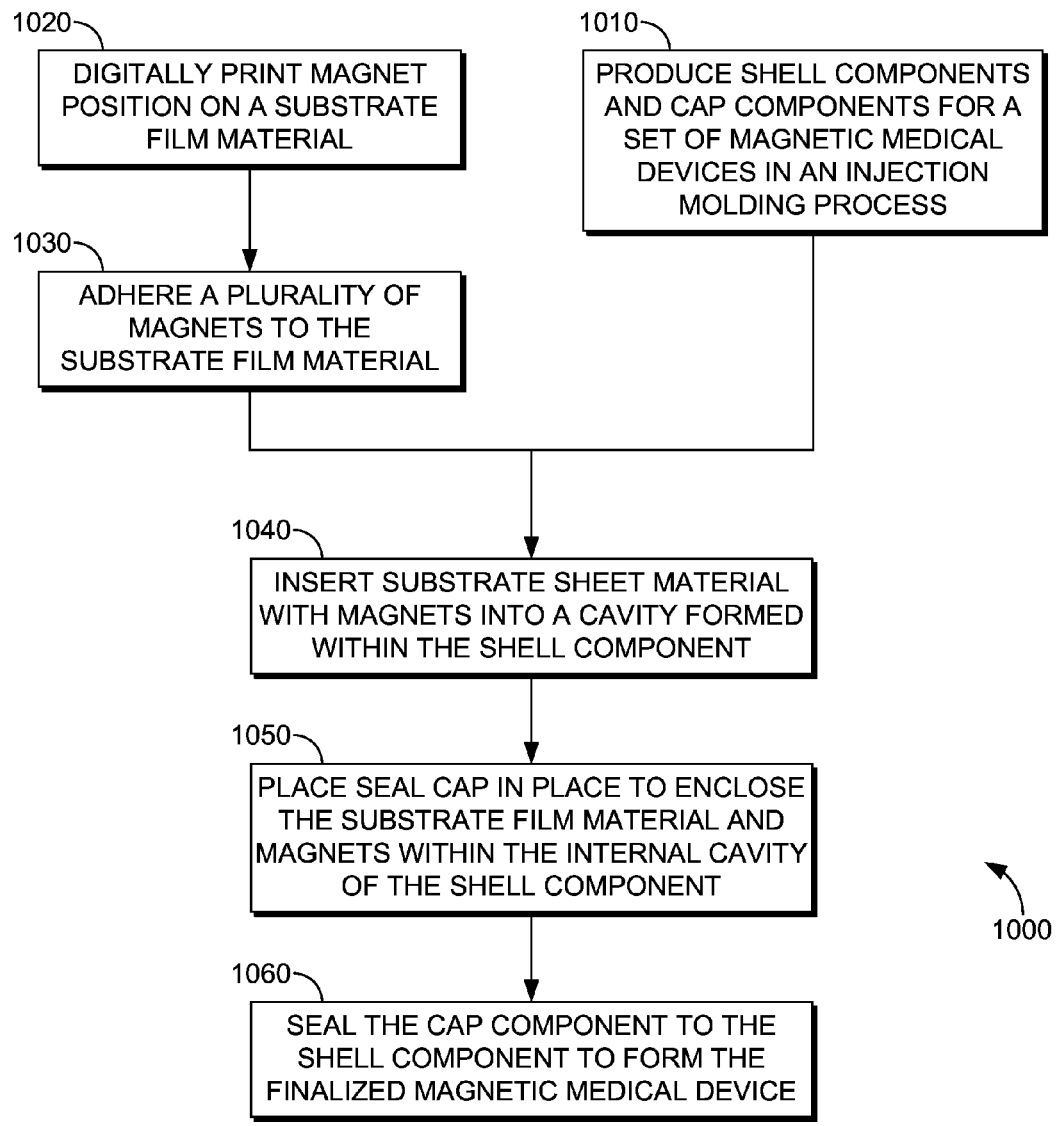
FIG. 10 is a flow diagram depicting a method for manufacturing the magnetic medical device in accordance with the present invention.

Finally, FIG. 10 depicts a flow chart 1000 outlining a method of manufacturing a set of magnetic medical devices/vaginal dilators in accordance with embodiments of the present invention. For instance, at step 1010, a set of vaginal dilators may be produced in a "clean room," sanitized and free from microbes or other contaminants, via an injection molding process. The set may comprise vaginal dilators of varying sizes. For example, the set may comprise five vaginal dilators having active diameter sizes ranging from 0.5 inches to 1.5 inches. The passive diameter size may vary for each of the corresponding active diameter sizes, or in the alternative, may be the same for all the vaginal dilators in the set. For example, in the latter case, the 0.5 inch active diameter vaginal dilator may comprise a passive diameter of 2 inches, and the 1.5 inch active diameter vaginal dilator may also comprise a passive diameter of 2 inches.

Each iteration of the injection molding process may produce the set of vaginal dilators at one time. Alternatively, each iteration of the injection molding process may produce a predefined quantity of each size of a vaginal dilator at a time. If each iteration of the molding process produces the set of vaginal dilators, the mold may comprise a plurality of molding cavities ranging in sizes suitable for production of respectively sized shell components and cap components from a medical grade polycarbonate material. In the alternative, a mold comprising a predefined quantity of molding cavities of the same size may be provided for each vaginal dilator size in the set of vaginal dilators, wherein the molding cavities comprise a shell component molding cavity and a cap component molding cavity.

In parallel, or subsequently, at step 1020, a plurality of substrate films are produced for each of the vaginal dilators produced at step 1010, wherein each substrate film is printed with a magnet array map at a printing station. At step 1030, one or more magnets are adhered or affixed at respective positions on each of the substrate films having respective magnet array maps printed thereon. The magnet array maps are important because they ensure an even distribution of magnets throughout each substrate film to ensure the generation of an even negative magnetic field when the substrate film is rolled in to a cylindrically-shaped magnetic sleeve. Provided alternate means of production, the array maps may be replaced with an automated distributing means (e.g., computer-aided manufacturing or templates for configuring the magnets onto the film). As presented above, the negative magnetic field is generated by adhering each magnet on the substrate film with its positive pole always adhered to the substrate film, and its opposite negative pole always facing outwardly. It is contemplated, however, that various configurations of the magnet and film remain within the scope of the present invention as long as the negative poles face radially outward with respect to the dilator.

At step 1040, the substrate films are rolled into magnetic sleeves and inserted into the shell components produced at step 1010. At step 1050, each respective magnetic sleeve is enclosed into its respective shell component produced in step 1010, by placing a corresponding cap component to each shell component also produced in step 1010. Finally, at step 1060, each cap component is bonded, ultrasonically or adhesively, to each respective shell component.

Due to the different anatomical characteristics of women using the magnetic medical devices in accordance with aspects of the present invention, the magnetic medical devices may be provided as a set of vaginal dilators comprising two or more vaginal dilators of different sizes. A particular female patient may determine a suitably-sized magnetic medical device by first trying the smallest size and gradually moving up in size until a suitably-sized magnetic medical device is found. Although the steps described herein are portrayed from the perspective of the female patient, any or all steps can also be performed by a medical professional (e.g., doctor, nurse, therapist) providing care to the female patient.

In order to determine a suitably-sized vaginal dilator, the patient may first need to thoroughly wash and dry each magnetic medical device in the set of magnetic medical devices. Then, starting from the smallest sized magnetic medical device, the patient may lubricate the magnetic medical device and insert it into her vaginal canal making sure that the magnetic vaginal dilator is inserted as deeply as it is comfortable; repeating the process with each progressively larger magnetic medical device until a suitably-sized medical device is found.

Once the suitably-sized medical device is found, selecting the suitably-sized device for treatment. For each treatment session, the patient is advised to lubricate the selected magnetic medical device prior to insertion into her vaginal canal. Once the magnetic medical device is inserted into the patient's vaginal canal, the patient must maintain the magnetic medical device in its inserted position for a predetermined length of treatment time for maintain contact of the vaginal canal with the negative magnetic field. Once the predetermined length of treatment time has lapsed, removing the magnetic medical device from the patient's vaginal canal. Each treatment session may range, for example, from 10 minutes to 45 minutes, depending on the needs for the particular patient. Furthermore, treatment sessions may be repeated as needed, until desired results, or desired levels of relief from the chronic conditions is reached.

Many different arrangements of the various components depicted, as well as components not shown, are possible without departing from the scope of the claims below. Embodiments of the technology have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

The invention claimed is:
1. A magnetic vaginal dilator comprising:
    a shell component that presents a smooth outer surface having an ogive top end and an elongate cylindrical middle portion that tapers outwardly proximate to an open bottom end, the shell component having an inner surface that defines a cavity that is accessible at the open bottom end;
    a substrate film having one or more magnets affixed thereto and disposed within the cavity of the shell component such that the one or more magnets extend circumferentially about the inner surface at the middle portion of the shell component; and a cap component sized to fit into the open bottom end of the shell component and seal the substrate film within the cavity of the shell component.

2. The magnetic vaginal dilator of claim 1, wherein the shell component and the cap component comprise a medical grade thermoplastic polymer material.

3. The magnetic vaginal dilator of claim 2, wherein the medical grade thermoplastic polymer material comprises polycarbonate.

4. The magnetic vaginal dilator of claim 1, wherein the one or more magnets comprise neodymium earth magnets.

5. The magnetic vaginal dilator of claim 1, wherein the one or more magnets present a general cylindrical shape.

6. The magnetic vaginal dilator of claim 5, wherein the one or more magnets have a diameter from 0.1 inches to 0.5 inches and a height from 0.05 and to 0.1 inches.

7. The magnetic vaginal dilator of claim 6, wherein the one or more magnets have a diameter of 0.25 inches and a height of 0.0625 inches.

8. The magnetic vaginal dilator of claim 5, wherein the one or more magnets have a positive polar portion and a negative polar portion, wherein the negative polar portion of the one or more magnets is directed radially inward toward the shell component when the substrate film is within the cavity of the shell component.

9. The magnetic vaginal dilator of claim 1, wherein a diameter of the elongate cylindrical middle portion ranges between 0.5 inches and 1.5 inches.

10. The magnetic vaginal dilator of claim 1, wherein a diameter of the bottom end ranges between 1 inch and 2 inches.

11. The magnetic vaginal dilator of claim 1, wherein a total length of the magnetic vaginal dilator ranges between 1.5 inches and 8 inches.

12. The magnetic vaginal dilator of claim 1, wherein the cap component is ultrasonically sealed to the shell component.

13. The magnetic vaginal dilator of claim 1, wherein the substrate film comprises a thickness ranging between 0.002 inches to 0.008 inches.

14. The magnetic vaginal dilator of claim 13, wherein the substrate film comprises a thermoplastic polymer material.

15. The magnetic vaginal dilator of claim 14, wherein the thermoplastic polymer material comprises polyester.

16. The magnetic vaginal dilator of claim 1, wherein the substrate film is rolled to form a magnetic sleeve.

17. The magnetic vaginal dilator of claim 16, wherein the one or more magnets includes an evenly distributed array of magnets, and wherein the magnetic sleeve is configured to evenly distribute a magnetic field about at least a portion of the smooth outer surface.

18. The magnetic vaginal dilator of claim 1, wherein the inner surface, proximate to the open bottom end, presents an internal flange, and wherein the cap component is configured to engage the internal flange when fit into the open bottom end.

19. A magnetic vaginal dilator comprising:
  a shell component that presents an outer surface having an arcuate top end and an elongated cylindroid middle body that tapers radially outward proximate to an open bottom end, the open bottom end presenting a cavity defined by an inner surface of the shell component and further presenting an internal flange;
  a polymer sheet having a plurality of magnets affixed thereon and rolled into a sleeve, the sleeve being disposed into the cavity of the shell component such that the plurality of magnets is coaxially positioned around the inner surface along at least a portion of the elongated cylindroid middle body; and
  a cap component sized to fit into the open bottom end of the shell component and engage the internal flange to seal the polymer sheet within the cavity of the shell component.

* * * * *